(12) United States Patent
Beardsley

(10) Patent No.: US 6,193,691 B1
(45) Date of Patent: Feb. 27, 2001

(54) CATHETER SYSTEM

(75) Inventor: Timothy Beardsley, Kingston, MA (US)

(73) Assignee: Depuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/281,546

(22) Filed: Mar. 30, 1999

(51) Int. Cl.$^7$ ................................................. A61M 5/178
(52) U.S. Cl. ........................................................ 604/164.01
(58) Field of Search .................................... 604/160, 164, 604/170, 43, 44, 45, 264

(56) References Cited

U.S. PATENT DOCUMENTS

| | | | |
|---|---|---|---|
| 3,225,762 | 12/1965 | Guttman | 128/214 |
| 4,576,589 | 3/1986 | Kraus et al. | 604/8 |
| 4,578,057 | 3/1986 | Sussman | 604/9 |
| 4,613,324 | 9/1986 | Ghajar | 604/49 |
| 4,632,668 | 12/1986 | Wilson, Jr. et al. | 604/8 |
| 4,636,200 | 1/1987 | Vaillancourt | 604/170 |
| 4,723,942 | 2/1988 | Scott | 604/164 |
| 4,784,638 | 11/1988 | Ghajar et al. | 604/49 |
| 4,821,716 | 4/1989 | Ghajar et al. | 128/303 B |
| 4,931,056 | 6/1990 | Ghajar et al. | 606/130 |
| 4,950,232 | 8/1990 | Ruzicka et al. | 604/43 |
| 4,970,926 | 11/1990 | Ghajar et al. | 83/468.94 |
| 5,104,388 * | 4/1992 | Quakenbush | 604/264 |
| 5,180,387 | 1/1993 | Ghajar et al. | 604/266 |
| 5,312,357 * | 5/1994 | Buijs et al. | 604/164 |
| 5,788,713 | 8/1998 | Dubach et al. | 606/130 |
| 5,951,568 * | 9/1999 | Schatz | 606/108 |

* cited by examiner

*Primary Examiner*—Glenn K. Dawson
*Assistant Examiner*—Catherine Serke
(74) *Attorney, Agent, or Firm*—Nutter, McClennen & Fish, LLP

(57) ABSTRACT

A catheter system includes a elongate catheter having a longitudinal slit for facilitating removal of a rigid stylet after manipulating the catheter to a desired position. In one embodiment, the stylet is contained within the catheter prior to use. The stylet is removed by bending the catheter such that a proximal portion of the stylet protrudes from the slit to allow a surgeon to grasp and remove the stylet from the catheter. In an exemplary embodiment, the catheter system includes a ventricular catheter for draining fluid from a patient's brain ventricle.

18 Claims, 5 Drawing Sheets

CATHETER SYSTEM

CROSS-REFERENCE TO RELATED APPLICATIONS

Not Applicable.

STATEMENT REGARDING FEDERALLY SPONSORED RESEARCH

Not Applicable.

FIELD OF THE INVENTION

The present invention relates generally to bioimplantable devices, and more particularly, to a system for introducing a catheter into the ventricle of a patient's brain.

BACKGROUND OF THE INVENTION

Catheters of various types are used to drain fluid from different areas of the body of a patient. One application of such catheters is for the treatment of head traumas where excess fluid accumulates in the patient's cranium. Another application of fluid drainage catheters is in the treatment of hydrocephalus, a condition in which cerebrospinal fluid (CSF) collects in the ventricles of the brain of a patient. In each case, an increased fluid volume within the cranium results in an increase in intracranial pressure. If these conditions are left untreated, the pressure levels resulting from the fluid build up can result in serious medical conditions, including compression of the brain tissue, impaired blood flow, and tissue ischemia.

To relieve the pressure, a drainage catheter can be inserted into the cranium to promote fluid drainage. One known technique for inserting the distal end of a catheter into a brain ventricle is described in U.S. Pat. No. 5,312,357 to Buijs et al. First and second incisions are made in the patient's scalp and a burr hole, which is aligned with the second incision, is formed in the patient's skull. An elongate needle is inserted into an opening in the catheter, which is coupled to a length of tubing, for tunneling the catheter/tubing assembly under the patient's scalp from the first incision to the second incision. The needle is then removed from the catheter and from the patient's scalp via the first incision for allowing the catheter to be manipulated such that it is aligned with the burr hole. The needle is then re-inserted into the catheter for guiding it into a brain ventricle. After the catheter is inserted to a desired depth, the needle is removed from the catheter.

While the technique described by Buijs et al. may provide a means to implant a catheter into a brain ventricle, there are certain concomitant drawbacks. In particular, a surgeon is required to assemble the needle and catheter two separate times. And for each time the needle must be inserted into the catheter, the opening in the catheter must be located. In addition, the needle may damage surrounding brain tissue if the needle is removed while within the skull. Further, any buckling of the catheter as the needle exits the catheter can damage brain tissue.

It would, therefore, be desirable to provide a system and method that allows rapid and safe implantation of a catheter into a patient's brain ventricle.

SUMMARY OF THE INVENTION

The present invention provides a system for implanting a catheter into a patient's body. Although the invention is primarily shown and described with reference to implanting a drainage catheter into a patient's ventricle, it is understood that the system has other applications as well.

In one embodiment, a catheter system includes a catheter for draining fluid from a patient's ventricle via surgical tubing coupled to the catheter. The elongate catheter has proximal and distal ends with a first lumen formed in the catheter for removably capturing a rigid stylet. The catheter includes a second lumen for providing a fluid drainage path. Prior to use, the stylet is contained within the first lumen in the catheter. A longitudinal slit is formed along a predetermined length of the catheter with the slit extending from an outer surface of the catheter into the first lumen. The stylet can be removed from the first lumen by bending the catheter such that a portion of the stylet protrudes from the slit. The exposed portion of the stylet can be grasped by a surgeon to remove the stylet from the catheter after it is positioned in the ventricle.

In an exemplary technique for implanting a brain ventricular catheter, first and second incisions are initially formed in the patient's scalp and a burr hole, which is generally coincident with the second incision, is created in the patient's skull. The rigid nature of the stylet facilitates tunneling of the catheter under the scalp from the first incision to the second incision. The catheter and the surgical tubing are then manipulated such that the catheter is generally perpendicular to the skull. The distal end of the catheter is inserted into the patient's cranium to a desired depth and position. The catheter is maintained in position while a proximal portion of the catheter is bent thereby forcing a part of the rigid stylet to exit the catheter via the slit. A surgeon then removes the stylet from the catheter and secures the catheter and tubing in position.

BRIEF DESCRIPTION OF THE DRAWINGS

The invention will be more fully understood from the following detailed description taken in conjunction with the accompanying drawings, in which.

DETAILED DESCRIPTION OF THE INVENTION

The drawings are understood to be illustrative of the concepts disclosed herein to facilitate an understanding of the invention. Further, the drawings are not to scale, and the scope of the invention is not to be limited to the particular embodiments shown and described herein.

Figure 1:
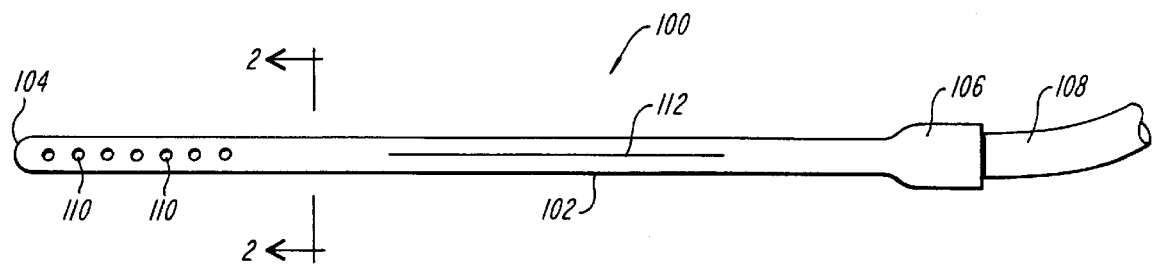
FIG. 1 is a side view of a catheter system in accordance with the present invention.
Figure 2:
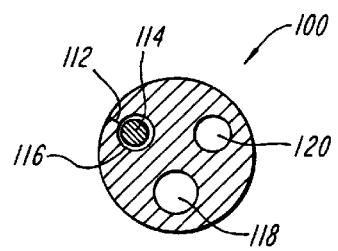
FIG. 2 is a cross-sectional view of the catheter system of FIG. 1 along line 2—2.
Figure 3:
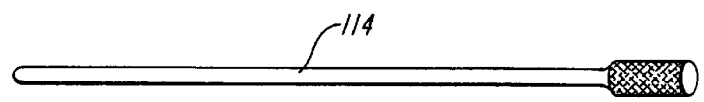
FIG. 3 is a side view of a stylet that forms a part of the catheter system of FIG. 1.

FIGS. 1–3 show a catheter system 100 in accordance with the present invention. The system 100 includes a catheter 102 having a distal end 104 adapted for implantation into a ventricle in a patient's brain and a proximal end 106 adapted for connection to a length of surgical tubing 108.

Alternatively, the catheter has a length that is optimized for discharging fluid directly from the proximal end 106 of the catheter. The distal end 104 of the catheter includes a series of apertures 110 that provide a path for fluid, e.g., CSF, to flow into the catheter for drainage from the cranium. A longitudinal slit 112 is formed in the catheter 102 to facilitate removal of a rigid stylet 114 from the catheter. The catheter system 100 allows a surgeon to rapidly tunnel the catheter under the patient's scalp and safely insert the distal end 104 of the catheter into a brain ventricle. In addition, the rigid stylet 114 can be removed from the catheter after manipulating the distal end 104 of the catheter to a desired position while minimizing the risk of tissue damage during the stylet removal process.

In an exemplary embodiment, the catheter 100 includes multiple lumens to allow fluid drainage, to house the stylet, and to provide a signal pathway. A first lumen 116 is sized to capture the stylet 114. The longitudinal slit 112 formed in the catheter 102 extends from an outer surface into the first lumen 116 to allow the stylet to be removed from the catheter 102, as described below.

A second lumen 118, which is in fluid communication with the drainage apertures 110, extends from the distal end 104 of the catheter to the surgical tubing 108. The second lumen 118 provides a path for CSF, for example, to exit the cranium and flow through the catheter and the surgical tubing 108 for ultimate discharge and external collection and/or absorption in the peritonium. In one embodiment, a valve is implanted under the scalp in communication with the surgical tubing to regulate the intracranial pressure.

A third lumen 120 in the catheter provides a passageway for a lead or conductor, for example, to allow a signal from a probe to propagate to remote monitoring equipment. Exemplary probes include pressure and temperature sensors that generate electrical signals indicative of conditions at the sensor site.

In general, it is preferred that the slit be formed in a lumen that does not provide a fluid drainage path since it is possible that the fluid may leak from the slit. Therefore, the catheter should include at least one lumen for containing the stylet and at least one lumen for providing fluid drainage. It is understood, however, that single lumen catheters, which house a rigid stylet as well provide fluid drainage, are within the scope of the invention.

Figure 4:
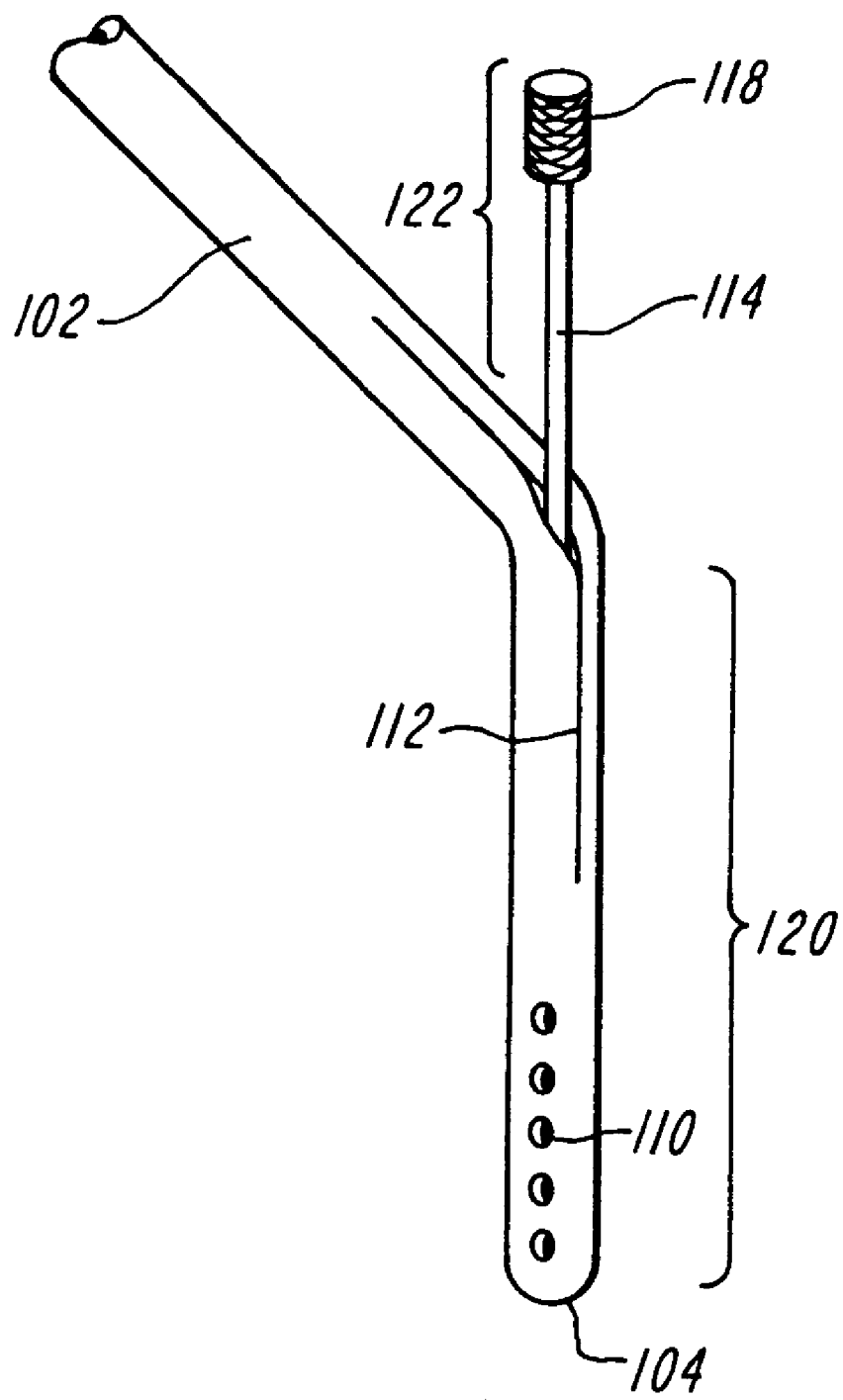
FIG. 4 is a pictorial diagram of the stylet of FIG. 3 being removed from the catheter system of FIG. 1.

As shown in FIG. 4, the longitudinal slit 112 in the first lumen 116 allows a surgeon to remove the stylet 114 upon selectively bending the catheter 102. More particularly, by maintaining the position of a distal region 120 of the catheter 102 and deforming it at a point along the slit 112, a proximal portion 122 of the stylet 114 exits the first lumen 116. To this end, the slit 112 should extend beyond a proximal tip 118 (FIG. 3) of the stylet 114 when the stylet is contained within the catheter 102. The exposed portion 122 of the stylet 114 is readily graspable by a surgeon to facilitate its removal from the catheter.

In an exemplary embodiment, the proximal tip 118 of the stylet includes a geometry and/or surface texture for enhancing the surgeon's ability to securely grip the stylet. In one embodiment, the proximal tip 118 of the stylet is knurled.

It is understood that the overall dimensions of the system components can vary. The catheter 102 has an exemplary length that ranges from about twenty centimeters to about fifty centimeters. The length of the slit 112 can range from about two centimeters to about fifteen centimeters. And the diameter of the stylet can range from about 0.5 millimeters to about 1.5 millimeters.

Figure 5:
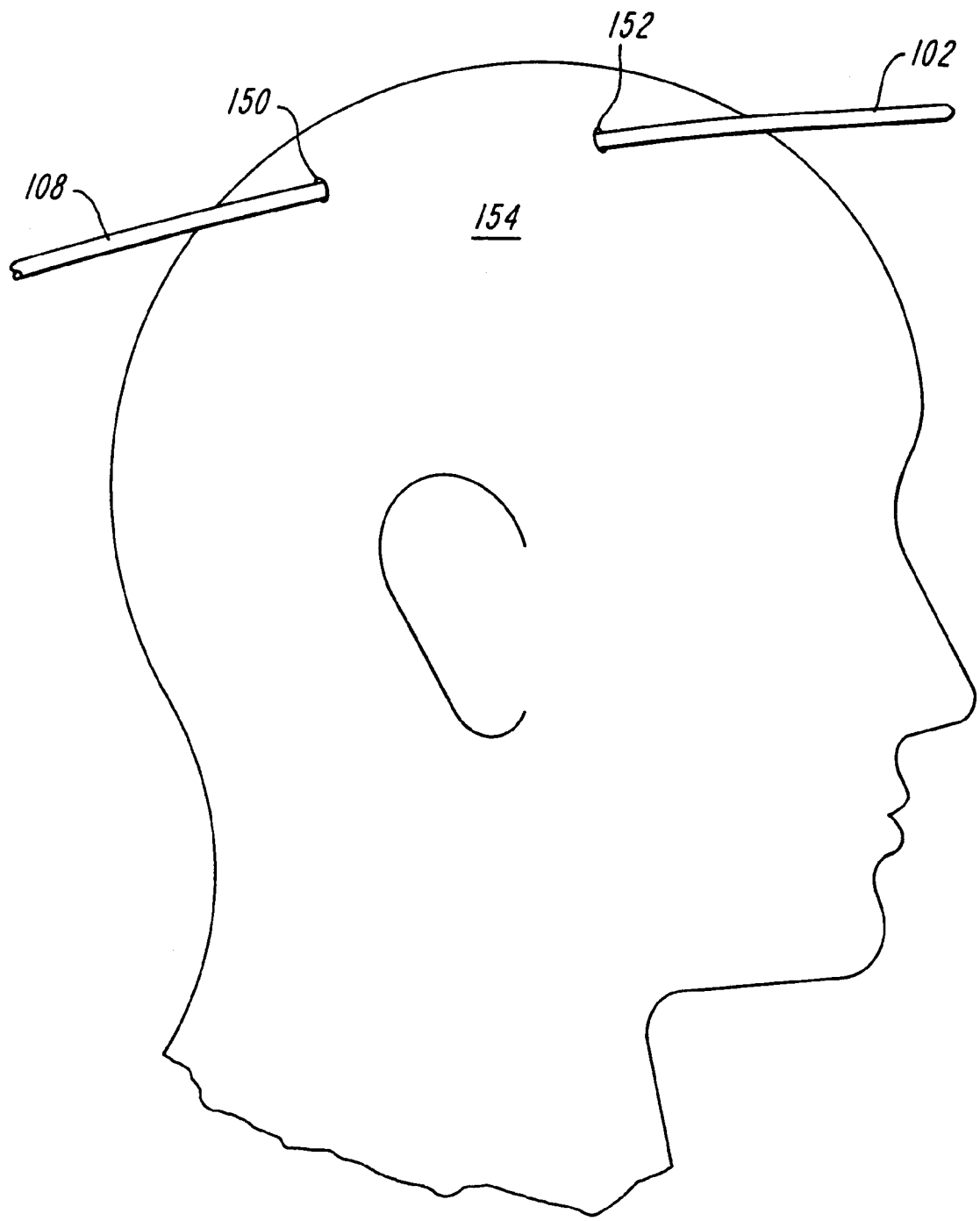
FIG. 5 is a pictorial diagram of the catheter system of FIG. 1 being tunneled under a patient's scalp.
Figure 6:
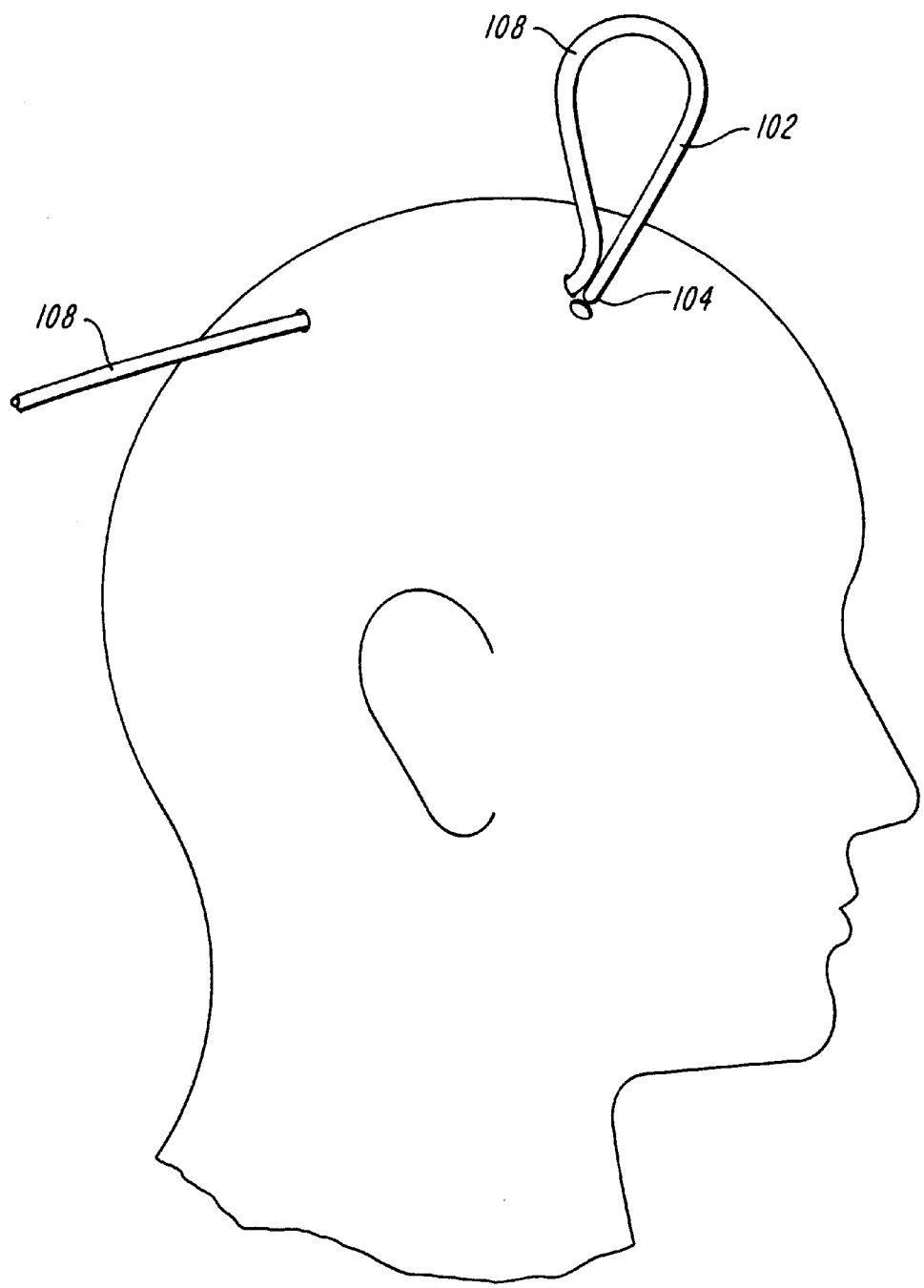
FIG. 6 is a pictorial diagram of the catheter system of FIG. 1 being inserted into a burr hole in the patient's skull.
Figure 7:
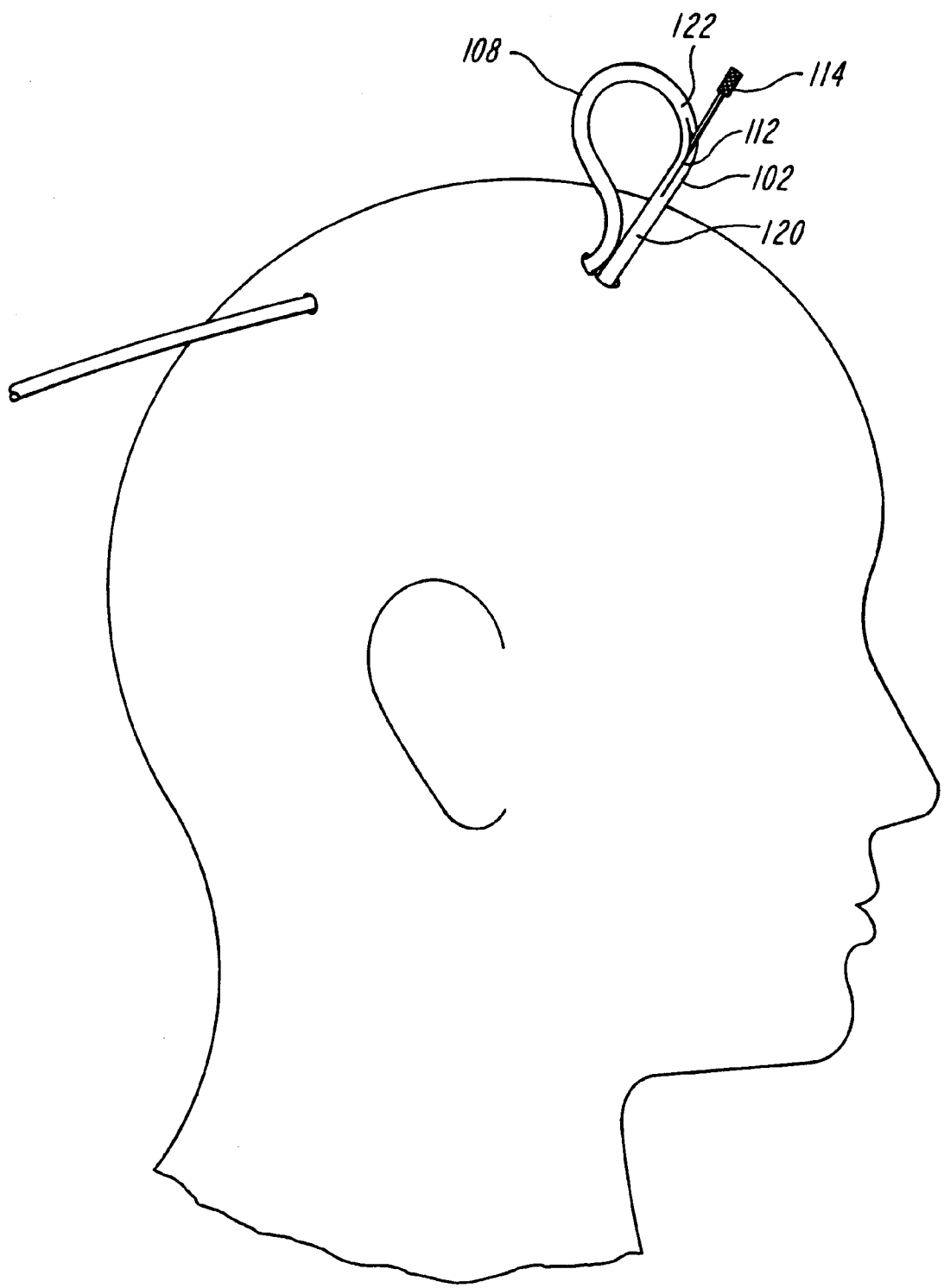
FIG. 7 is a pictorial diagram of the catheter system of FIG. 1 with the stylet of FIG. 3 being removed.

FIGS. 5–7 show an exemplary technique for using the catheter system of FIGS. 1–3 to treat acute head trauma. It is understood that the invention is also applicable to the treatment of hydrocephalus. Initially, first and second incisions 150,152 are formed in a patient's scalp 154 at predetermined locations and a burr hole (not shown) is formed in the skull proximate the second incision. The catheter 102, with the rigid stylet 114 (FIGS. 2–4) contained therein, is tunneled under the scalp from the first incision 150 to the second incision 152 (FIG. 5). The stylet 114 imparts a rigidity to the catheter 102 that enhances the ability of the surgeon to advance the catheter under the scalp.

The catheter 102, along with a desired amount of surgical tubing 108, is extended from the second incision 152 so as to allow the catheter to be positioned generally upright in relation to the patient's skull (FIG. 6). The distal end 104 of the catheter is aligned with the burr hole in the skull to allow insertion of the catheter into the brain ventricle.

The catheter 102, which is still rigid due to the stylet 114, is inserted into the patient's brain to a desired depth. In one embodiment, the distal end of the catheter is positioned so as to promote drainage of fluid from the brain ventricle. After the catheter 102 is manipulated to a desired position, a portion of the catheter adjacent the skull is used to maintain the catheter in position within the ventricle. A proximal portion of the catheter is bent such that a proximal portion 122 of the stylet protrudes from the slit 112 in the catheter (FIG. 7). The surgeon then grasps the textured, exposed proximal tip 118 of the stylet 114 and removes it from the catheter.

After the stylet 114 is removed from the catheter, any slack in the surgical tubing 108 can be removed and the catheter/tubing assembly can be secured in position, such as by conventional suturing techniques.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A catheter system, comprising:
    an elongate catheter including a distal end and a proximal end, the catheter having a first lumen and an elongate, longitudinal slit formed along a predetermined length of the catheter, the slit extending from an outer surface of the catheter into the first lumen; and
    a rigid stylet removably captured within the first lumen in its entirety such that a proximal end of the slit extends proximally beyond a proximal end of the stylet.

2. The system according to claim 1, wherein the catheter is a ventricular catheter.

3. The system according to claim 1, wherein the stylet facilitates tunneling of the catheter under a patient's scalp.

4. The system according to claim 1, wherein the stylet is adapted to be captured within the first lumen of the catheter until the catheter is implanted within a patient's ventricle.

5. The system according to claim 1, wherein the catheter further includes a second lumen in fluid communication with drainage apertures located at the distal end of the catheter.

6. The system according to claim 5, wherein the catheter further includes a third lumen for providing a signal path for signals generated by a probe at the distal end of the catheter.

7. The system according to claim 1, wherein the slit is from about 2 centimeters to about 15 centimeters in length.

8. The system according to claim 1, wherein the stylet has a length that ranges from about 20 to about 50 centimeters.

9. The system according to claim 1, wherein the proximal end of the stylet is textured to promote secure handling of the stylet.

10. The system according to claim 1, further comprising a length of surgical tubing coupled to the proximal end of the catheter.

11. The system according to claim 1, wherein the stylet is removable from the first lumen by bending the catheter along the slit.

12. The system according to claim 1, wherein the slit is located on a generally distal region of the catheter.

13. A catheter system for draining CSF from a patient, comprising:
   a ventricular catheter including
      a distal end having apertures for draining the CSF;
      a proximal end for coupling to surgical tubing;
      a first lumen formed in a predetermined length of the catheter;
      an elongate, longitudinal slit extending from an outer surface of the catheter into the first lumen;
      a second lumen in fluid communication with the apertures and the proximal end of the catheter for allowing the CSF to drain from the patient; and
      a third lumen formed in the catheter for providing a passageway for a conductor that is adapted for carrying a signal from a probe located at the distal end of the catheter; and
   a rigid stylet removably captured in its entirety within the first lumen.

14. The system according to claim 13, wherein the slit is at least 2 centimeters in length.

15. The system according to claim 13, wherein the stylet is removable from the first lumen by bending the catheter.

16. A method for implanting a ventricular catheter, comprising:
   forming first and second incisions in a patient's scalp;
   forming a hole in the patient's skull proximate the second incision;
   tunneling a catheter under the scalp from the first incision to the second incision, the catheter having a rigid stylet entirely disposed within a lumen thereof;
   manipulating the catheter such that it is generally upright in relation to the skull;
   inserting the catheter into the patient's cranium;
   bending the catheter so as to force a portion of the rigid stylet disposed in the catheter to cause at least a portion of the stylet to exit a longitudinal slit in the catheter; and
   removing the stylet from the catheter.

17. The method according to claim 16, further including draining fluid from the cranium via a second lumen formed in the catheter.

18. The method according to claim 17, further including monitoring a physiological condition by inserting a probe into the cranium via a third lumen formed in the catheter.

* * * * *